United States Patent [19]

Aretz et al.

[11] Patent Number: 5,310,666
[45] Date of Patent: May 10, 1994

[54] PROCESS FOR THE ENANTIOSELECTIVE PREPARATION OF (β-1)-HYDROXYALKYLXANTHINES BY REDUCTION USING RHODOTORULA RUBRA

[75] Inventors: Werner Aretz, Königstein/Taunus; Harald Furrer, Hofheim am Taunus; Ulrich Gebert, Schlossborn; Heinz-Joachim Hinze, Wiesbaden, all of Fed. Rep. of Germany

[73] Assignee: Hoechst Aktiengesellschaft, Frankfurt am Main, Fed. Rep. of Germany

[21] Appl. No.: 975,996

[22] Filed: Nov. 13, 1992

Related U.S. Application Data

[63] Continuation of Ser. No. 631,400, Dec. 21, 1990, abandoned.

[30] Foreign Application Priority Data

Dec. 23, 1989 [DE] Fed. Rep. of Germany ....... 3942872

[51] Int. Cl.⁵ ............................................. C12P 17/18
[52] U.S. Cl. .................................... 435/119; 435/280; 435/822
[58] Field of Search ................. 435/280, 119, 822

[56] References Cited

U.S. PATENT DOCUMENTS 4,833,146 5/1989 Gerbert et al. ........................ 514/263

FOREIGN PATENT DOCUMENTS 1233405 2/1967 Fed. Rep. of Germany.
1235320 2/1967 Fed. Rep. of Germany.
2402908 7/1975 Fed. Rep. of Germany.
2330742 9/1975 Fed. Rep. of Germany.
0023032 1/1981 Fed. Rep. of Germany.
8700523 1/1987 Fed. Rep. of Germany.

OTHER PUBLICATIONS

ATCC Catalog of Fungi/Yeasts, p. 267 (1984).
Saucier et al., J. Biol. Chem 264: 6863-6869 (1989).
Smith et al., J. Chrom. 281: 281-287 (1983).
Davis et al., Appl. Env. Microbiology 48: 327-331 (1984).
Jones et al., Tetrahedron 42: 3351-3403 (1986).
Davis et al, Xenobiotica 12: 1001-1010 (1985).
Mitteilung, European Search Report, dated Jun. 17, 1992.

Primary Examiner—Douglas W. Robinson
Assistant Examiner—S. Saucier
Attorney, Agent, or Firm—Finnegan, Henderson, Farabow, Garrett & Dunner

[57] ABSTRACT

A *Rhodotorula rubra* strain has been found which reduces pentoxifylline to 100% to give the S-alcohol. Moreover, other oxoalkylxanthine derivatives can also be converted into the corresponding S-alcohol. The microbiologically obtained S-(+)-enantiomers can then be converted stereoselectively into the respective R-(−)-enantiomers. The corresponding S-alcohols and the R-alcohols obtained by enantioselective inversion of configuration cause an increase in cerebral blood flow.

8 Claims, No Drawings

PROCESS FOR THE ENANTIOSELECTIVE PREPARATION OF ($\beta$-1)-HYDROXYALKYLXANTHINES BY REDUCTION USING RHODOTORULA RUBRA This application is a continuation of application Ser. No. 07/631,400 filed Dec. 21, 1990, now abandoned.

Oxoalkylxanthines are employed for the treatment of peripheral, cerebral and ocular vascular disorders. The best-known substance from this group is pentoxifylline [1-(5-oxohexyl)-3,7-dimethylxanthine]. In the human organism, pentoxifylline is primarily reduced to give a mixture of enantiomeric alcohols.

Davis et al. [*Appl. Environ. Microbiol.* 48, 327 (1984); *Xenobiotica* 15, 1001 (1985)] have furthermore found 13 cultures of microorganisms which either reduce pentoxifylline to the alcohol or cleave the side chain at the carbonyl group and form the corresponding carboxylic acids. Davis et al. further describe that the strain *Rhodotorula rubra* (ATCC 20129) forms the S-enantiomer of the alcohol corresponding to pentoxifylline. However, using this strain only a 56% reaction is achieved to give the S-alcohol in 40% preparative yield in the course of 72 hours.

A *Rhodotorula rubra* strain has now surprisingly been found with which pentoxifylline can be reduced to about 100% to give the S-alcohol in about 62% preparative yield in the same time. Moreover, other oxoalkylxanthine derivatives can also be converted into the corresponding S-alcohol. The corresponding S-alcohols and the R-alcohols obtained by enantioselective inversion of configuration cause an increase in cerebral blood flow.

The invention thus relates to a process for the enantioselective preparation of ($\omega$-1)-hydroxyalkylxanthines, which comprises reducing ($\omega$-1)-oxoalkylxanthine derivatives of the formula I

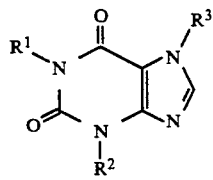

(I)

in which $R^1$, $R^2$ and $R^3$, which can be identical or different, are chosen from the group comprising the substituents $CH_3$—$CO$—$(CH_2)_m$— and ($C_1$ to $C_6$)-alkyl, where one of the substituents of the group must be $CH_3$—$CO$—$(CH_2)_m$, m is an integer from 2 to 6, and ($C_1$ to $C_6$)-alkyl can be straight-chain or branched, or in which $R^1$ is $CH_3$—$CO$—$(CH_2)_4$—, $R^2$ is $CH_3$— and $R^3$ is $CH_3$—$O$—$CH_2$—, to the respective S-(+)-enantiomers containing the substituent (S)—$CH_3$—$CH(OH)(CH_2)_m$—, where m has the abovementioned meaning, or to the compound in which $R^1$ is (S)—$CH_3$—$CH(OH)$—$(CH_2)_4$—, $R^2$ is $CH_3$— and $R^3$ is $CH_3$—$O$—$CH_2$—, by incubation with *Rhodotorula rubra* DSM 5436.

If not stated otherwise, the ($\omega$-1)-oxoalkylxanthines of the formula I used as starting materials in this process are known, inter alia, from German Auslegeschriften 1,233,405 and 1,235,320 or German Offenlegungsschriften 2,330,742 and 2,402,908 or can easily be prepared by known processes.

The strain *Rhodotorula rubra* was deposited in the German Collection of Microorganisms and Cell Cultures GmbH on 11.07.89 under the number DSM 5436 according to the rules of the Budapest Treaty. Instead of the strain deposited, its mutants and variants can also be employed according to the invention if, of course, they are able to carry out the reduction of the compounds of the formula I.

The abovementioned compounds of the formula I can be used as substrates. Compounds of the formula I characterised above are preferred in which only one of the substituents $R^1$, $R^2$ and $R^3$ is the group $CH_3$—$CO$—$(CH_2)_m$—, or in which m is the number 2 to 5 and the alkyl group has 1 to 4 carbon atoms, or in which $R^2$ is a methyl or ethyl radical. Compounds of said formula I are furthermore preferred in which $R^2$ is a $C_1$ to $C_4$-alkyl radical and $R^1$ and $R^3$ are the group $CH_3$—$CO$—$(CH_2)_m$— or a $C_1$ to $C_4$-alkyl radical, where m is 2 to 5. The compounds of said formula I are also preferred in which $R^1$ and $R^3$ are the group $CH_3$—$CO$—$(CH_2)_m$, where m is 3 to 5, or $C_1$ to $C_3$-alkyl and $R^2$ is a methyl or ethyl radical. Further preferred compounds of the characterised formula I are those in which m is the number 2. Very good results were also achieved with the compounds of said formula I in which $R^1$ and $R^3$ are $CH_3$—$CO$—$(CH_2)_2$— or a $C_1$ to $C_4$-alkyl radical and $R^2$ is also a $C_1$ to $C_4$-alkyl radical.

However, the compounds of the formula I are particularly preferably reduced in which a) $R^1$ is $CH_3$—$CO$—$(CH_2)_4$— and $R^2$ is $CH_3$— and $R^3$ is $CH_3$—$(CH_2)_2$— or b) $R^1$ and $R^2$ are $CH_3$— and $R^3$ is $CH_3$—$CO$—$(CH_2)_4$— or c) $R^1$ is $CH_3$—$CO$—$(CH_2)_4$— and $R^2$ is $CH_3$— and $R^1$ is $CH_3$—$O$—$CH_2$— or d) $R^1$ is $CH_3$—$CO$—$(CH_2)_4$— and $R^2$ and $R^3$ are $CH_3$— or e) $R^1$ and $R^2$ are $CH_3(CH_2)_3$— and $R^3$ is $CH_3CO(CH_2)_2$— f) $R^1$ is $CH_3$—$CO$—$(CH_2)_3$— and $R^2$ is $CH_3$— and $R^3$ is $CH_3$—$(CH_2)_2$— or g) $R^1$ is $CH_3$—$CO$—$(CH_2)_5$— and $R^2$ and $R^3$ are $CH_3$—.

Said compounds can be utilised individually or in mixtures of the strain DSM 5436.

The addition of the substrate can be carried out at any desired time during the growth or the stationary phase of *Rhodotorula rubra* SM 5436. The strain can essentially be cultured aerobically, preferably with shaking, in all nutrient solutions suitable for growth, at 25° to 32° C. Such nutrient media can rapidly be found by the person skilled in the art without inventive merit.

A procedure can advantageously be used in which the substrate of the formula I is added to the microorganism culture after about 5 to 20 hours' growth in a nutrient solution, in particular after 8 to 17 hours. The amount of substrate added can vary within wide ranges, but it is preferably 0.5 to 10 g/l of nutrient solution, in particular 0.7 to 1.2 g/l of nutrient solution. The nutrient solution preferably contains glucose, soya bean meal and yeast extract as a carbon and nitrogen source. It is incubated in the abovementioned temperature range over a period of 70 to 355 hours, it being possible to monitor the progress of the reaction by means of TLC.

Up to 100% of the substrate concerned can in this way be reacted to give the respective S-(+)-enantiomer.

The invention furthermore relates to a process for the inversion of the configuration of the microbiologically obtained S-(+)-enantiomers. In this process, the respective R-(−)-enantiomers which contain an (R)—CH$_3$—CH(OH)—(CH$_2$)$_m$ radical in one of the positions R$^1$, R$^2$ or R$^3$ of the formula I are prepared stereoselectively.

An advantageous process comprises, for example, converting an S-(+)-enantiomer into the R-(−)-enantiomer which is still present as the carboxylic acid ester using a tertiary phosphine, preferably triphenylphosphine, a carboxylic acid, preferably benzoic acid and a dialkyl azodicarboxylate, preferably diethyl azodicarboxylate, in an aprotic solvent, preferably tetrahydrofuran and converting the carboxylic acid ester into the compounds having an R—(−)—CH$_3$—CH(OH)—(CH$_2$)$_m$ radical in one of the positions R$^1$, R$^2$ or R$^3$ of the formula I by solvolysis according to known methods, in particular by methanolysis in the presence of potassium carbonate.

A further process, which is also advantageous, comprises converting the hydroxyl group on the asymmetric carbon atom of the S-(+)-enantiomers into an organic sulfonic acid ester, preferably a methanesulfonic acid ester or a p-toluenesulfonic acid ester, which is directly converted into the R-(−)-enantiomers by nucleophilic substitution and inversion of configuration or into the compounds having an (R)—CH$_3$—CH(OH)—(CH$_2$)$_m$ radical in one of the positions R$^1$, R$^2$ or R$^3$ of the formula I via one of their carboxylic acid esters and its subsequent solvolysis. The sulfonic acid esters are prepared by known methods by reaction of the S-(+)-hydroxyalkylxanthines with organic sulfonyl halides, preferably methanesulfonyl chloride and p-toluenesulfonyl chloride, in aprotic solvents, preferably pyridine and dichloromethane, if appropriate in the presence of a base, such as triethylamine.

Suitable agents for the nucleophilic substitution of the sulfonic acid esters are, for example, alkali metal salts of aliphatic carboxylic acids, preferably cesium propionate, in aprotic solvents such as dimethylformamide or dimethyl sulfoxide. The solvolysis of the resulting carboxylic acid esters is carried out in alcoholic or aqueous solvents, preferably in methanol, in the presence of basic substances, such as, for example, potassium carbonate.

The invention further relates to the novel substances 7-methoxymethyl- 3-methyl-1-(5-oxohexyl)xanthine and racemic 1-(5-hydroxyhexyl)-7-methoxymethyl-3-methylxanthine and the corresponding R- and S-enantiomers.

The compounds can be employed for the treatment of vascular disorders.

The examples shown in the following are used to illustrate the invention further.

EXAMPLES

Percentage data relate to the weight, if not stated otherwise.

1. Medium and growth conditions

| Pre- and main culture medium | |
|---|---|
| Glucose | 2% |
| Soya bean meal | 0.5% |
| Yeast extract | 0.5% |
| NaCl | 0.5% |
| K$_2$HPO$_4$ | 0.5% |
| pH 7.0 | |

A 2 l Erlenmeyer flask containing 500 ml of nutrient solution which is inoculated with a washing from the slant tubes is used as the preculture. After an incubation period of 72 hours at 28° C. and at a shaking frequency of 250 rpm, the main culture is inoculated with an inoculum of 10% from this preculture. The main culture is carried out in a 12 l fermenter using 9 l of nutrient solution at 28° C., an aeration rate of 0.1 vpm and a stirrer speed of 300 rpm.

TABLE

| Name of the starting material | Structure (Formula I) | | | Reaction period (hours) | Degree of reaction (%) | Stereospecificity of the reduction |
|---|---|---|---|---|---|---|
| | R$^1$ | R$^2$ | R$^3$ | | | |
| 3-Methyl-1-(5-oxohexyl)-7-propylxanthine | CH$_3$CO—(CH$_2$)$_4$ | CH$_3$ | (CH$_2$)$_2$—CH$_3$ | 88 | 100 | >96% |
| 1,3-Dimethyl-7-(5-oxohexyl)xanthine | H$_3$C | CH$_3$ | (CH$_2$)$_4$—COCH$_3$ | 250 | 100 | >96% |
| 7-Methoxymethyl-3-methyl-1-(5-oxohexyl)xanthine | CH$_3$CO—(CH$_2$)$_4$ | CH$_3$ | CH$_2$—O—CH$_3$ | 160 | 100 | >97% |
| 3,7-Dimethyl-1-(5-oxohexyl)xanthine (pentoxifylline) | CH$_3$CO(CH$_2$)$_4$ | CH$_3$ | CH$_3$ | 96 | 100 | >98% |
| 1,3-Dibutyl-7-(3-oxobutyl)-xanthine | C$_4$H$_9$ | C$_4$H$_9$ | (CH$_2$)$_2$COCH$_3$ | 186 | 100 | >96% |

2. Reduction of the oxoalkylxanthines

After 8–17 hours' growth in the main culture step, the sterile-filtered substrate (10 g in 200 ml of 50% strength ethanol) is added to the cell suspension. Results are summarized by way of example in the table. The progress of the reduction is monitored by means of TLC. At the end, the culture solution is filtered off and the culture filtrate is lyophilized.

3. TLC analysis

2 µl each of culture filtrate are applied to HPTLC plates (silica gel 60 F 245) and developed in the mobile phase chloroform-ethanol (9:1). Evaluation is carried out at 270 nm with the aid of a TLC scanner.

4. Characterization of the reduced final products and their inversion of configuration:

The structure of all compounds described below was checked by elemental analysis and IR and $^1$H NMR spectra. The absolute configuration and the enantiomeric purity were determined by means of the Mosher esters of the enantiomeric hydroxyalkylxanthines with S-(−)-methoxytrifluoromethylphenyl acetic acid ($^1$H or $^{19}$F NMR spectra). The enantiomeric purity of the alcoholic final products was also determined by gas chromatography after derivatisation with S-(−)-1-phenylethyl isocyanate.

a) S-(+)-1-(5-Hydroxyhexyl)-3,7-dimethylxanthine 579 g of lyophilizate (from the reduction of 65 g of pentoxifylline using *Rhodotorula rubra*, DSM 5436) are suspended in 3 l of isopropyl alcohol, 750 g of celite are added and the mixture is filtered through a Seitz pressure filter. The filter cake is treated by extraction with a total of 12 l of isopropyl alcohol and the combined filtrates are concentrated on a rotary evaporator in a water jet vacuum. The residue is taken up in dichloromethane, washed with 2N sodium hydroxide solution, 1N hydrochloric acid and water, dried and concentrated. The crude product is purified by chromatography in a medium pressure column on silica gel (particle size 20–45 μm) and dichloromethane/ethanol (volume ratio 98/2) as the eluent. After bulb tube distillation at 140°–150° C. bath temperature and 0.3 mbar, a yield of 40.8 g (62.3% of theory) is obtained.

Melting point: 110° C.
Enantiomeric excess (e.e.) >98%
$[\alpha]_D^{20} = 5.7°$ (c=6.7 g $C_2H_5OH$)
Analysis: calc.: C 55.7%, H 7.19%, N 19.99%. found: C 55.8%, H 7.34%, N 20.17%.

b) S-(+)-1-(5-Hydroxyhexyl)-3-methyl-7-propylxanthine 560 g of lyophilizate (from the reduction of 65 g 1-(5-oxohexyl)-3-methyl-7-propylxanthine with *Rhodotorula rubra*, DSM 5436) were worked up, purified and characterized analogously to a).

Yield: 32 g (49% of theory)
Melting point: 81°–82° C.
e.e. >97%
$[\alpha]_D^{20} = +4.6°$ (c=6.6, $C_2H_5OH$)
Analysis: calc.: C 58.42%, H 7.84%, N 18.17%. found: C 58.54%, H 8.02%, N 18.15%.

c) 1. S-(+)-7-(5-Hydroxyhexyl)-1,3-dimethylxanthine 2. 7-(4-Hydroxybutyl)-1,3-dimethylxanthine 430 g of lyophilizate (from the reduction of 30 g of 7-(5-oxohexyl)-1,3-dimethylxanthine with *Rhodotorula rubra* DSM 5436) were worked up, purified and characterized analogously to a). Two substances were obtained.

For the 1st: Yield: 6.4 g (21.1% yield)
Melting point: 93° C.
e.e. >96%
$[\alpha]_D^{20} = +8.5°$ (c=2.3; $C_2H_5OH$)
Analysis: calc.: C 55.7%, H 7.19%, N 19.99%. found: C 55.69%, H 7.24%, N 19.65%.

For the 2nd: Yield: 2.3 g (8.3% yield)
Melting point: 113°–114° C.
Analysis: calc.: C 52.37%, H 6.39%, N 22.21%. found: C 52.35%, H 6.59%, N 22.05%.

d) S-(+)-1-(5-Hydroxyhexyl)-7-methoxymethyl-3-methyl xanthine

Preparation of the prochiral 7-methoxymethyl-3-methyl-1-(5-oxohexyl)xanthine as a starting material: 21.0 g (0.1 mol) 7-methoxymethyl-3-methylxanthine (prepared from 3-methylxanthine and methoxymethyl chloride or methoxymethyl 4-toluenesulfonate analogously to the procedures described in detail in DE-OS 3,525,801; $C_8H_{10}N_4O_3$ (MW=210.2), melting point 251°–253° C.,Analysis: calc.: C 45.71%, H 4.80%, N 26.66%; found: C 45.56%, H 4.78%, N 26.60%) were dissolved in 500 ml of dimethylformamide, 15.2 g (0.11 mol) of potassium carbonate and 14.8 g (0.11 mol) of 1-chloro-5-hexanone were added and the reaction mixture was stirred vigorously at about 110° C. for 18 hours. It was then cooled and evaporated under reduced pressure, the solid residue was partitioned between 1N sodium hydroxide solution and chloroform and the organic phase was separated off, washed with water until free from salt, dried over sodium sulfate and freed from solvent under reduced pressure. Recrystallisation from ethyl acetate with the addition of petroleum ether at the boiling point yielded 27.1 g (87.9% of theory) of analytically pure ketone having a melting point of 106°–107° C.

$C_{14}H_{20}N_4O_4$ (MW=308.3)
Analysis: calc.: C 54.54%, H 6.54%, N 18.17%. found: C 54.59%, H 6.57%, N 17.99%.

By reducing 12.3 g (0.04 mol) of this oxohexyl compound with 0.76 g (0.02 mol) of sodium borohydride in 100 ml of anhydrous methanol at reflux temperature in the course of 2 hours, concentrating the mixture under reduced pressure, taking up the evaporation residue in chloroform, washing the solution four times with a little water, drying over sodium sulfate, evaporating the solvent under reduced pressure and thoroughly stirring the solid product in diethyl ether, 8.3 g (66.8% of theory) of racemic 1-(5-hydroxyhexyl)-7-methoxymethyl-3-methylxanthine having a melting point of 63°–65° C. were obtained in analytically pure form.

$C_{14}H_{22}N_4O_4$ (MW=310.4)
Analysis: calc.: C 54.18%, H 7.15%, N 18.05%. found: C 54.07%, H 7.21%, N 17.97%.

240 g of lyophilizate from the reduction of 10 g (0.032 mol) of 7-methoxymethyl-3-methyl-1-(5-oxohexyl)xanthine with *Rhodotorula rubra*, DSM 5436, were subjected to rigorous freeze-drying and then extracted with tert. butyl methyl ether in a Soxhlet apparatus for 8 hours, it being possible to isolate 8 g (79.5%) of oily crude product. For the sake of simplicity, the crude product was purified by chromatography on a 43 cm long silica gel column having a diameter of 2.8 cm, after application of the crude produce dissolved in toluene lipophilic impurities being eluted with toluene and then the S-(+)-enantiomeric alcohol adhering to the silica gel being washed out first with pure tert. butyl methyl ether and then the latter mixed with acetone in the volume ratio 7:3. The crystalline pure product obtained in this manner contained ¼ mol of water of crystallisation according to elemental analysis.

$C_{14}H_{22}N_4O_4 \times \frac{1}{4}H_2O$ (MW=314.9)
Yield: 6.11 g (59.8% of theory)
Melting point: 65°–66° C.
e.e.: >98%
$[\alpha]_D^{20}$: +4.86° (c=0.5 in dichloromethane)
Analysis: calc.: C 53.41%, H 7.20%, N 17.79%. found: C 53.37%, H 7.11%, N 17.83%.

e) S-(+)-1,3-Di-n-butyl-7-(3-hydroxybutyl)xanthine 2.5 g of lyophilizate (from the reduction of 0.25 g of 1,3-di-n-butyl-7-(3-oxobutyl)xanthine (melting point: 84° C.) with *Rhodotorula rubra*, DSM 5436) were worked up, purified and characterized analogously to a).

Yield: 0.15 g

Melting point: 68°–69° C.
$[\alpha]_D^{20}$: =+36.3° (c=3, $C_2H_5OH$)

Enantiomeric excess (e.e.) >96%
Analysis: calc.: C 60.69%, H 8.39%, N 16.65%. found: C 61.01%, H 8.59%, N 16.23%.

For comparison, racemic 1,3-di-n-butyl-7-(3-hydroxybutyl)xanthine (melting point=52° C.) was prepared by reduction of 1,3-di-n-butyl-7-(3-oxobutyl)xanthine with NaBH₄ analogously to d).

f)
S-(+)-1-(4-Hydroxypentyl)-3-methyl-7-n-propylxanthine 2.7 g of lyophilizate (from the reduction of 0.25 g of 1-(4-oxopentyl)-3-methyl-7-n-propylxanthine with *Rhodotorula rubra*, DSM 5436) were worked up, purified and characterized analogously to a).
Yield: 0.17 g
Melting point: 90°–91° C.
$[\alpha]_D^{20}: = +5.8°$ (c=3.4, C₂H₅OH)
Enantiomeric excess (e.e.) >98%
Analysis: calc.: C 57.13%, H 7.53%, N 19.03%. found: C 57.29%, H 7.68%, N 18.70%.

For comparison, racemic 1-(4-hydroxypentyl)-3-methyl-7-n-propylxanthine (melting point: 88°–89° C.) was prepared by reduction of 1-(4-oxopentyl)-3-methyl-7-n-propylxanthine with NaBH₄ analogously to d).

g) S-(+)-1-(6-Hydroxyheptyl)-3,7-dimethylxanthine 3 g of lyophilizate (from the reduction of 0.25 g of 1-(6-oxoheptyl)-3,7-dimethylxanthine (melting point: 122° C.) with *Rhodotorula rubra*, DSM 5436) were worked up, purified and characterized analogously to Example a).
Yield: 0.18 g
Melting point: 79°–81° C.
$[\alpha]_D^{20}: = +4.2°$ (c=3.5, C₂H₅OH)
e.e. >96%
Analysis: calc.: C 57.13%, H 7.53%, N 19.03%. found: C 56.88%, H 7.93%, N 18.86%.

Racemic 1-(6-hydroxyheptyl)-3,7-dimethylxanthine (melting point: 76°–77° C.) was prepared for comparison by reduction of 1-(6-oxoheptyl)-3,7-dimethylxanthine with NaBH₄ analogously to d).

h) R-(−)-1-(5-Hydroxyhexyl)-3,7-dimethylxanthine 36 g of diethyl azodicarboxylate in 120 ml of absolute tetrahydrofuran are added dropwise at room temperature to a solution of 29.8 g of S-(+)-1-(5-hydroxyhexyl)-3,7-dimethylxanthine, 17.8 g of benzoic acid and 53.1 g of triphenylphosphine in 120 ml of absolute tetrahydrofuran during the course of 15 min. After stirring at room temperature for 8 hours, the mixture is concentrated at reduced pressure and the residue (150 g) is purified in a medium pressure column on silica gel (20–45 μm particle size and 6 nm pore size) using dichloromethane/methanol in the volume ratio 98:2 as the eluent.

78 g of crude R-(−)-1-(5-benzoyloxyhexyl)-3,7-dimethylxanthine are produced, which are stirred at room temperature as a solution in 300 ml of methanol together with 5 g of potassium carbonate for 48 hours. After concentrating at reduced pressure, the residue is taken up using dichloromethane, the solid is filtered off and the solution is chromatographed as above, but using dichloromethane/methanol in the volume ratio 95:5. The clean fractions by thin-layer chromatography are distilled through a bulb tube at 150°–155° C. bath temperature and 0.3 mbar. A yield of 21.2 g (71.1% of theory) is obtained.
Melting point: 110° C.
$[\alpha]_D^{20}: = -5.6°$ (c=6.7, C₂H₅OH)
Enantiomeric excess (e.e.) >98%
Analysis: calc.: C 55.7%, H 7.19%, N 19.99%. found: C 55.63%, H 7.26%, N 19.91%.

i)
R-(−)-1-(5-Hydroxyhexyl)-3-methyl-7-propylxanthine

The preparation and subsequent purification are carried out analogously to h) from 19 g of S-(+)-1-(5-hydroxyhexyl)-3-methyl-7-propylxanthine
Yield: 14.7 g (77.4% of theory)
Melting point: 81°–82° C.
$[\alpha]_D^{20}: = -4.5°$ (c=6.3, C₂H₅OH)
e.e. >98%
Analysis: calc.: C 58.42%, H 7.84%, N 18.17%. found: C 58.36%, H 8.08%, N 18.22%.

j) R-(−)-7-(5-Hydroxyhexyl)-1,3-dimethylxanthine

Reaction and subsequent purification are carried out analogously to h) starting from 3.4 g of S-(+)-7-(5-hydroxyhexyl)-1,3-dimethylxanthine.
Yield: 2.4 g (70.4% of theory)
Melting point: 93° C.
$[\alpha]_D^{20}: = -8.4°$ (c=2.2, C₂H₅OH)
e.e. >96%
Analysis: calc.: C 55.7%, H 7.19%, N 19.99%. found: C 55.73%, H 7.17%, N 19.73%.

k) R-(−)-1,3-Di-n-butyl-7-(3-hydroxybutyl)xanthine

The reaction, subsequent purification and characterization were carried out analogously to Example h starting from 6.8 g of S-(+)-1,3-di-n-butyl-7-(3-hydroxybutyl)xanthine.
Yield: 3.8 g
Melting point: 67°–68° C.
$[\alpha]_D^{20} = -34.6°$ (c=2, C₂H₅OH)
e.e. >96%
Analysis: calc.: C 60.69%, H 8.39%, N 16.65%. found: C 60.30%, H 8.57%, N 16.64%.

l)
R-(−)-1-(4-Hydroxypentyl)-3-methyl-7-n-propylxanthine

The reaction, subsequent purification and characterization were carried out analogously to Example h starting from 3.3 g of S-(+)-1-(4-hydroxypentyl)-3-methyl-7-n-propylxanthine.
Yield: 2.2 g
Melting point: 90° C.
$[\alpha]_D^{20}: = -6.2°$ (c=0.8, C₂H₅OH)
e.e. >97%
Analysis: calc.: C 57.13%, H 7.53%, N 19.03%. found: C 56.78%, H 7.46%, N 18.83%.

m) R-(−)-1-(6-Hydroxyheptyl)-3,7-dimethylxanthine

The reaction, subsequent purification and characterization were carried out analogously to Example h starting from 11.6 g of S-(+)-1-(6-hydroxyheptyl)-3,7-dimethylxanthine.
Yield: 6.2 g
Melting point: 82°–84° C.
$[\alpha\alpha]_D^{20}: = -4.8°$ (c=1.6 C₂H₅OH)
e.e. >96%
Analysis: calc.: C 57.13%, H 7.53%, N 19.03%. found: C 56.77%, H 7.78%, N 19.01%.

We claim:

1. A process for the enantioselective preparation of an (ω-1)-hydroxyalkylxanthine which comprises incubating the compound of the formula I

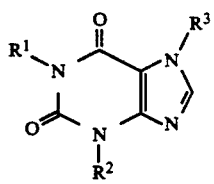

in which
R$^1$, R$^2$ and R$^3$, which can be identical or different, are selected from the group consisting of the substituents CH$_3$—CO—(CH$_2$)$_m$— and (C$_1$ to C$_6$)-alkyl, where one of the substituents of the group must be CH$_3$—CO—(CH$_2$)$_m$, m is an integer from 2 to 6, and (C$_1$ to C$_6$)-alkyl can be straight-chain or branched, or
in which
R$^1$ is CH$_3$—CO—(CH$_2$)$_4$—, R$^2$ is CH$_3$— and R$^3$ is CH$_3$—O—CH$_2$—, with *Rhodotorula rubra* DSM 5436 to prepare S-(+)-(ω-1)-hydroxyalkylxanthine, and recovering said S-(+)-(ω-1)-hydroxyalkylxanthine.

2. The process as claimed in claim 1, wherein the compound in which only one of the substituents R$^1$, R$^2$ and R$^3$ is the group CH$_3$—CO—(CH$_2$)$_m$ is employed as the compound of the formula I.

3. The process as claimed in claim 1, wherein the compound in which
a)
  R$^1$ is CH$_3$—CO—(CH$_2$)$_4$— and
  R$^2$ is CH$_3$— and
  R$^3$ is CH$_3$—(CH$_2$)$_2$— or
b)
  R$^1$ and R$^2$ are CH$_3$— and
  R$^3$ is CH$_3$—CO—(CH$_2$)$_4$— or
c)
  R$^1$ is CH$_3$—CO—(CH$_2$)$_4$— and
  R$^2$ is CH$_3$— and
  R$^3$ is CH$_3$—O—CH$_2$— or
d)
  R$^1$ is CH$_3$—CO—(CH$_2$)$_4$— and
  R$^2$ and R$^3$ are CH$_3$— or
e)
  R$^1$ and R$^2$ are CH$_3$ (CH$_2$)$_3$— and
  R$^3$ is CH$_3$CO(CH$_2$)$_2$—
f)
  R$^1$ is CH$_3$—CO—(CH$_2$)$_3$— and
  R$^2$ is CH$_3$— and
  R$^3$ is CH$_3$—(CH$_2$)$_2$— or
g)
  R$^1$ is CH$_3$—CO—(CH$_2$)$_5$— and
  R$^2$ and R$^3$ are CH$_3$—
is employed as the compound of the formula I.

4. The process as claimed in claim 1, wherein the incubation is carried out at 25° to 32° C.

5. The process as claimed in claim 1, which further comprises preparing the respective R-(−)-enantiomer by reacting said S-(+)-(ω-1)-hydroxyalkylxanthine in an aprotic solvent with a tertiary phosphine, a carboxylic acid and a dialkyl azodicarboxylate and converting the reaction product into the compound of the formula I in which one of the substituents R$^1$, R$^2$ or R$^3$ is R—(−)—CH$_3$—CH(OH)—(CH$_2$)$_m$ by solvolysis.

6. The process as claimed in claim 5, wherein the tertiary phosphine is triphenylphosphine, the carboxylic acid is benzoic acid, the dialkyl azodicarboxylate is diethyl azodicarboxylate, the aprotic solvent is tetrahydrofuran, and the solvolysis is carried out in the form of a methanolysis in the presence of potassium carbonate.

7. The process as claimed in claim 1, which further comprises the stereoselective preparation of the respective R-(−)-enantiomer by:
a) reacting said S-(+))-(ω-1)-hydroxyalkylxanthine with an organic sulfonyl halide in an aprotic solvent to form an organic sulfonic acid ester of said S-(+)-(ω-1)-hydroxyalkylxanthine;
b) further reacting said organic sulfonic acid ester of S-(+)-(ω-1)-hydroxyalkylxanthine with an alkali metal salt of an aliphatic carboxylic acid in an aprotic solvent to form an aliphatic carboxylic acid ester of R-(−)-(ω-1)-hydroxyalkylxanthine; and
c) converting said aliphatic carboxylic acid ester of R-(−)-(ω-1)-hydroxyalkylxanthine into the compound of the formula I as claimed in claim 1 in which one of the substituents R$^1$, R$^2$ or R$^3$ is R—(−)CH$_3$—CH(OH)—(CH$_2$)$_m$, by solvolysis in an alcoholic or aqueous solvent in the presence of a basic substance.

8. The process of claim 7, wherein the organic sulfonyl halide as in a) is methanesulfonyl chloride or p-toluenesulfonyl chloride, the aprotic solvent is pyridine or dichloromethane and the alkali metal salt of aliphatic carboxylic acids as in b) is cesium propionate, the aprotic solvent is dimethylformamide or dimethyl sulfoxide and the solvent as in c) is methanol and the basic substance is potassium carbonate.

* * * * *

UNITED STATES PATENT AND TRADEMARK OFFICE
CERTIFICATE OF CORRECTION

PATENT NO. : 5,310,666
DATED : May 10, 1994
INVENTOR(S) : Aretz et al.

It is certified that error appears in the above-indentified patent and that said Letters Patent is hereby corrected as shown below:

On the title page, item [54] and in column 1, line 4, in the title change the Greek symbol for beta (β) to the Greek symbol for omega (ω).

In column 1, line 4, change the Greek symbol for beta to the Greek symbol for omega.

Signed and Sealed this

Eighteenth Day of April, 1995

Attest:

BRUCE LEHMAN

Attesting Officer

Commissioner of Patents and Trademarks